United States Patent [19]

Chou et al.

[11] 4,115,644

[45] Sep. 19, 1978

[54] PROCESS FOR PREPARING PURE CEFAMANDOLE FROM ALKALI METAL AND AMMONIUM SALTS THEREOF

[75] Inventors: Ta Sen Chou; Gary D. Zintgraff, both of Indianapolis, Ind.

[73] Assignee: Eli Lilly and Company, Indianapolis, Ind.

[21] Appl. No.: 834,633

[22] Filed: Sep. 19, 1977

[51] Int. Cl.$^2$ .......................................... C07D 501/12
[52] U.S. Cl. .................................................. 544/20
[58] Field of Search .......................................... 544/20

[56] References Cited

U.S. PATENT DOCUMENTS

| | | | |
|---|---|---|---|
| 3,947,415 | 3/1976 | Tensmeyer | 544/20 |
| 4,028,355 | 6/1977 | Blackburn | 544/20 |
| 4,029,655 | 6/1977 | Cise | 544/20 |

*Primary Examiner*—Nicholas S. Rizzo
*Attorney, Agent, or Firm*—Ralph W. Ernsberger; Arthur R. Whale

[57] ABSTRACT

Passing a solution, buffered to a pH of from about 3.5 to about 4.5, of an alkali metal or ammonium salt of cefamandole through a bed of an adsorbent resin depending on van der Waals forces for adsorption followed by acidification to a pH of about 2.0 with a non-oxidizing inorganic acid yields pure crystalline cefamandole, which can be separated and dried, or partitioned into a preferential solvent from which crystalline sodium cefamandole can be recovered.

7 Claims, No Drawings

PROCESS FOR PREPARING PURE CEFAMANDOLE FROM ALKALI METAL AND AMMONIUM SALTS THEREOF

BACKGROUND OF THE INVENTION

1. Field of the Invention

This invention is concerned with a chemical process. More particularly, the instant invention involves a process for removing inpurities from alkali metal and ammonium salts of cefamandole and the subsequent conversion of such salts to pure crystalline cefamandole.

2. Prior Art

Cefamandole is a member of the class of antibiotics known as cephalosporins. Many of the cephalosporins are highly useful antiinfectives and are widely used for the treatment of disease in man and animals. Cefamandole bodes well to become one of the more useful members of this group of semi-synthetic antibiotics inasmuch as it has superior activity against a wide range of pathological organisms.

Crystalline lithium and ammonium salts of cefamandole can be prepared readily from cefamandole synthesized from 7-amino-cephalosporanic acid (7ACA) or described in U.S. Pat. No. 3,641,021. While sodium and potassium salts of cefamandole can also be prepared from such starting material, they are not crystalline; they are amorphous. Neither lithium nor ammonium cations were thought to be medically preferred. On the other hand, either sodium or potassium salts are medically suitable for parenteral administration, and of these, sodium is preferred. It was discovered, however, that crystalline sodium cefamandole could be prepared from highly pure cefamandole; cefamandole from which the impurities, from the reaction converting the 7ACA to cefamandole, had been removed. A process for the preparation of crystalline sodium cefamandole from highly pure cefamandole is described in U.S. patent application Ser. No. 642,922, now U.S. Pat. No. 4,054,738.

Accordingly, it is an object of this invention to provide a process for preparing cefamandole of sufficient purity for conversion to crystalline sodium cefamandole.

SUMMARY

It has now been discovered that cefamandole of sufficient purity for conversion to crystalline sodium cefamandole can be prepared by a process comprising the following steps:

(a) an alkali metal or ammonium salt of cefamandole is dissolved in water;
(b) the solution of (a) is buffered to a pH of from about 3.5 to about 4.5 with a suitable buffer solution;
(c) a bed of an adsorbent resin depending on van der Waals forces for its adsorption capacity is conditioned by passing therethrough a volume of an appropriate buffer solution;
(d) the solution of (b) is passed through the resin bed of (c) and chased with a volume of the same buffer solution employed for conditioning the resin bed;
(e) the effluent from the resin bed and the buffer chaser are combined and acidified to a pH of about 2.0 with a non-oxidizing inorganic acid;
(f) the acidified solution of (e) is chilled and stirred precipitating pure crystalline cefamandole, or, alternatively, the pure cefamandole is partitioned from the solution of (e) into a suitable solvent.

DESCRIPTION OF THE PREFERRED EMBODIMENTS

It has now been discovered that pure crystalline cefamandole can be prepared by a process wherein an alkali metal or ammonium salt of cefamandole is dissolved in water; the aqueous solution of cefamandole is acidified to a pH of from about 3.5 to about 4.5 by adding thereto a buffer solution; the buffered cefamandole solution is passed through a bed of adsorbent resin having a large active surface (Macro-porosity) promoting van der Waals adsorption and having weak electrolyte activity and which has been conditioned previously by flushing with a buffer solution; the crystalline cefamandole acid is precipitated from the effluent from the adsorption resin by adjusting the effluent pH to about 2.0 with a non-oxidizing inorganic acid; and the resulting crystals from the acidified effluent are separated.

The useful method of this invention provides a means of preparing crystalline cefamandole acid from which crystalline sodium cefamandole, a highly effective and desirable antibiotic, can be readily and efficiently produced.

Cefamandole is a new antibiotic useful in the treatment of pathological infections in man and animals. It is a member of the well-known family of antibiotics, known as cephalosporins, that have gained wide-spread use as agents for the treatment of disease. It is described in U.S. Pat. No. 3,641,021 issued on Feb. 8, 1972.

Cefamandole, in its acid form, has the following structural formula

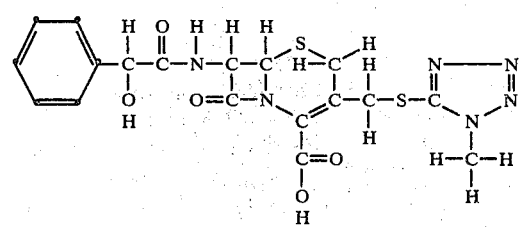

Chemically, cefamandole is described as 7-D-mandelamido-3-(1-methyl-1,2,3,4-tetrazolo-5-thiomethyl)-$\Delta^3$-cephem-4-carboxylic acid. Cefamandole can also be classified, along with the penicillins and other cephalosporins, as a $\beta$-lactam-type-antibiotic. Such antibiotics are characterized by a common $\beta$-lactam nucleus, to wit:

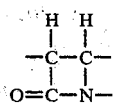

which in the case of the penicillins is fused into a thiazolidine ring and in the case of the cephalosporins is fused into a dehydrothiazine ring.

In common with many of the $\beta$-lactam-type-antibiotics, cefamandole is more stable chemically and physically in its crystalline form than in its amorphous form. And, in preparing useful pharmaceutical dosage forms it is highly desirable to employ the most stable form of the antibiotic.

Cefamandole in its acid form is not readily soluble in water. Inasmuch as the pharmaceutical dosage form of choice is one for parenteral administration, the most desired form of cefamandole is a crystalline water soluble salt thereof.

In the useful process of this invention an alkali metal or ammonium salt of cefamandole is employed as the starting material. The process is illustrated with lithium cefamandole, one of the alkali metal salts. Sodium or potassium, other alkali metals, or ammonium could be utilized. Such salts of cefamandole are water soluble, and in this process are preferably dissolved in deionized water.

The pH of an aqueous solution of lithium cefamandole is adjusted to from about 3.5 to about 4.5 by adding to such a solution a buffer solution comprised of an acid and an acid salt. Typical buffer solutions useful in this method include: citric acid-sodium citrate solution, acetic acid-sodium acetate solution, phosphoric acid-sodium phosphate solution, and, boric acid-sodium borate solution. A 0.1 molar citric acid-sodium citrate solution is a preferred buffer solution for use in the method of this invention. Other buffer solutions which are operative in this process are known to those skilled in the art. Neither the composition of the buffer solution nor its molarity is critical in this invention.

The buffered lithium cefamandole solution is passed through a bed of an adsorbent resin. Such a resin has a large active surface, characterized by a highly porous structure, and a weak electrolyte activity. The adsorptive capacity of such a resin depends primarily on van der Waals forces for the removal from a solution of substances, especially colored substances, which have an affinity for the active sites on the surface of the porous resin. There is a minimal ion exchange capacity present in such a resin. One especially preferred resin useful in this process is Duolite S-30 offered by the Diamond Shamrock Chemical Company, Resinous Products Division, P. O. Box 829, Redwood City, Calif. 94064. Duolite S-30 is described as a phenol-formaldehyde condensate having a large active surface (Macroporosity) and weak-electrolyte activity. The functional groups are phenolic hydroxyl groups. These adsorbent resins are described at length in the "Duolite Ion-Exchange Manual", prepared and edited by the technical staff of the Resinous Products Division, Diamond Shamrock Chemical Company. Other adsorbent resins having similar characteristics are operative in the useful process of this invention. Even those having secondary and tertiary amine functional groups such as Duolite S-37 can be employed, but with a resultant loss of yield.

The adsorbent resin is conditioned by passing a buffer solution, preferably the one employed to adjust the pH of the lithium cefamandole solution, through the bed prior to the introduction of such solution thereinto.

In the process of passing the acidified lithium cefamandole solution through the adsorbent resin bed some, if not all, of the impurities, along with up to 15 percent of the lithium cefamandole, are adsorbed on the resin. The effluent from the adsorption step contains 85 percent or more of the lithium cefamandole contained in the solution introduced into the bed.

The effluent is acidified to a pH of about 2 with a non-oxidizing inorganic acid such as hydrochloric, sulfuric, orthophosphoric, and the like. Such acids as chromic, nitric, and the like are not suitable and should not be used. Generally, organic acids are not strong enough to bring the pH down to 2. However, strong organic acids, such as trifluoro-, and tricloroacetic, oxalic acids, and the like can be used. At a pH of about 2, fine white crystals of cefamandole are crystallized from the acidified effluent, and are separated therefrom by filtration or centrifugation, or by other means known to those skilled in the art, and dried. The resulting cefamandole crystals are useful for preparing crystalline sodium cefamandole for parenteral administration.

Sodium cefamandole crystals can be prepared by dissolving the crystalline cefamandole, obtained from the useful process of this invention, in methanol and adding thereto a methanolic solution of a stoichemetric quantity of anhydrous sodium acetate (10% excess), and stirring the reaction mixture in an ice bath. Seeding may be used to hasten crystallization.

This invention is further illustrated by the following examples:

EXAMPLE 1

Crystalline cefamandole suitable for conversion to crystalline sodium cefamandole was prepared as follows:

Fifty-nine grams of lithium cefamandole were dissolved in one liter of deionized water. The resultant solution was acidified by adding 200 ml of 0.1 M citrate buffer solution thereto. The pH was 4.4.

Six hundred ml of Duolite S-30 resin were packed in a column 5 cm × 45 cm and conditioned by passing 200 ml of pH 4.4, 0.1 M, citrate buffer through the bed. The acidified lithium cefamandole solution was then passed through the resin bed and chased with 500 ml of the 0.1 M citrate buffer.

Then the total effluent from the resin bed was chilled in a wet ice pack, and, with constant stirring, the pH of the effluent was adjusted to 2.0 with 4% hydrochloric acid. Fine white crystals were precipitated as cefamandole hexahydrate which were filtered from the reaction mixture and dried overnight at 30° C. Fifty-two grams of cefamandole anhydrate were recovered for a yield of 85%.

EXAMPLE 2

Crystalline sodium cefamandole was obtained from the purified cefamandole prepared by the process of this invention by the following procedure.

Twenty grams of lithium cefamandole were dissolved in 200 ml of distilled water. The resultant solution was acidified with an acetate buffer to a pH of 4.4.

Two hundred milliliters of Duolite S-30 resin were placed in a column 3 cm × 30 cm and conditioned by passing 500 ml of an acetate buffer at pH 4.4 through the resin bed. Then the acidified lithium cefamandole solution was passed through the conditioned resin bed and chased with 250 ml of a pH 4.4 acetate buffer.

The resultant eluate was combined with 300 ml of ethyl acetate and the mixture was acidified with concentrated hydrochloric acid to pH 2.0. and stirred vigorously for 10 minutes. The mixture was then allowed to separate into two layers, the layers were separated and the ethyl acetate layer was washed once with an equal volume of deionized water.

The ethyl acetate was then stripped leaving a white solid which was taken up in 90 ml of methanol. Seven grams of sodium acetate (anhydrous) were dissolved in 60 ml of methanol and the resulting solution combined with the methanolic solution of the solids from the ethyl acetate layer. The resulting solution was placed in a wet ice pack and stirred. The solution was seeded with sodium cefamandole crystals, and in 20 minutes the crystallization of the sodium cefamandole was complete.

The yield was approximately 15 grams, or 75% of theory.

What is claimed is:

1. A method of preparing pure crystalline cefamandole from alkali metal and ammonium salts thereof comprising:
   (a) dissolving the cefamandole salt in water;
   (b) acidifying the solution from (a) with a buffer solution to a pH of from about 3.5 to about 4.5;
   (c) passing the solution from (b) through a bed of adsorbent resin having a large active surface (macroporosity) conducive to van der Waals adsorption and having weak electrolyte activity, said resin having been previously flushed with a buffer solution having a pH of from about 3.5 to about 4.5;
   (d) crystallizing the cefamandole from the effluent from said resin bed by adjusting the pH of said effluent to about 2; and,
   (e) separating the crystalline cefamandole from the acidified effluent.

2. The method of claim 1 wherein the buffer used in steps (b) and (c) is selected from the class consisting of a citric acid-sodium citrate solution, an acetic acid-sodium acetate solution, a phosphoric acid-sodium phosphate solution, and a boric acid-sodium borate solution.

3. The method of claim 1 wherein the buffer used in steps (b) and (c) is a 0.1 molar citric acid-sodium citrate solution.

4. The method of claim 1 wherein the resin used in step (c) is a macroporous phenol-formaldehyde condensate having phenolic hydroxyl functional groups.

5. The method of claim 1 wherein the acid used in step (d) is a non-oxidizing inorganic acid selected from the class consisting of hydrochloric, phosphoric, boric, hydrobromic, hydrofluoric, hydroiodic.

6. The method of claim 1 wherein the acid used in step (d) is hydrochloric.

7. The method of claim 1 wherein the cefamandole salt is lithium cefamandole.

* * * * *